United States Patent [19]
Lilja et al.

[11] Patent Number: 5,912,158
[45] Date of Patent: Jun. 15, 1999

[54] PROSTATE SPECIFIC ANTIGEN (PSA)-PROTEINASE INHIBITOR COMPLEXES

[76] Inventors: Hans Lilja, Holländarevägen 28, S-23600 Höllviken, Sweden; Ulf-Håkan Stenman, Heikelsvägen 10, SF-02700 Grankulla, Finland

[21] Appl. No.: 08/480,708

[22] Filed: Jun. 7, 1995

Related U.S. Application Data

[62] Division of application No. 07/956,509, filed as application No. PCT/FI91/00223, Jul. 22, 1991, Pat. No. 5,501,983.

[30] Foreign Application Priority Data

Jul. 23, 1990 [SE] Sweden .................................. 9002480

[51] Int. Cl.$^6$ ........................................................ C12N 9/64
[52] U.S. Cl. ............................ 435/226; 435/219; 530/350
[58] Field of Search ............................ 530/350; 435/226, 435/219

[56] References Cited

U.S. PATENT DOCUMENTS

| | | |
|---|---|---|
| 4,446,122 | 5/1984 | Chu et al. . |
| 5,599,677 | 2/1997 | Dowell et al. .............................. 435/7.4 |
| 5,599,686 | 2/1997 | DeFeo-Jones et al. .................... 435/23 |

FOREIGN PATENT DOCUMENTS

| | | |
|---|---|---|
| 0 160 228 | 11/1985 | European Pat. Off. . |
| 0 196 845 | 10/1986 | European Pat. Off. . |
| S62-46263 | 2/1987 | Japan . |

OTHER PUBLICATIONS

Stenman, U.–H. (1990). "Some Examples of the Effect of Immunoassay Design on Clinical Utility", Clinical Chemistry 36(6):1244–1245.

Schaller, J. et al. (1987). "Isolation, characterization and amino–acid sequence of γ–seminoprotein, a glycoprotein from human seminal plasma", Eur. J. Biochem. 170:111–120.

Christensson et al., Eur. J. Biochem. 194, 755–763 (Dec. 1990).

Stenman et al., Cancer Res. 51, 222–226 (1991).

Lilja et al., Clin. Chem. 37(9), 1618–1625 (1991).

DIALOG Information Service, File 351, WPIL, Accession No. 007662133 (WAKP) Wako Pure Chem. Ind. KK, "Determining antigen specific to human prostate gland ...", Japanese 63/215967 and 880908 8842 (Basic).

New York Academy of Sciences; N.Y. Annals, vol. 417 (1983) Chu et al., "Circulating Antibody to Prostate Antigen in Patients with Prostatic Cancer," (pp. 383–389).

Patent Abstracts of Japan, vol. 11, No. 233, P600, Abstract of Japanese Patent 62–46263, publ. 1987 Feb. 28; Chugai Pharmaceut. Co. Ltd.

Watt et al. (1986). Proc. Natl. Acad. Sci. USA 83:3166.

Lilja, H. (1985). J. Clin. Invest. 76:1899.

Primary Examiner—Kenneth R. Horlick
Attorney, Agent, or Firm—Venable, Baetjer, Howard & Civiletti, LLP

[57] ABSTRACT

Prostate specific antigen (PSA) is a protein that can form complexes with proteinase inhibitors such as $\alpha_1$-antichymotrypsin. The invention is characterized in that the measurement of the ratio of free PSA to PSA bound to proteinase inhibitors (free PSA:PSA-proteinase inhibitor complex) is useful in the diagnosis of patients with prostate cancer.

2 Claims, 10 Drawing Sheets

PROSTATE SPECIFIC ANTIGEN (PSA)-PROTEINASE INHIBITOR COMPLEXES

This application is a divisional of application Ser. No. 07/956,509, filed Mar. 19, 1993, U.S. Pat. No. 5,501,983, which is a 371 of PCT/FI91/00223, filed Jul. 22, 1991.

The present invention relates to an immunoassay of prostate-specific antigen (PSA), in which specific reagent materials (antibodies) are used that allow the measurement of free PSA as well as the PSA proteinase inhibitor complex.

It also relates to the use of free PSA and the PSA proteinase inhibitor complex and their ratio as a useful marker in diagnosis of patients with prostate cancer.

BACKGROUND OF THE INVENTION

The prostate specific antigen (PSA) was first purified from prostatic tissue (Wang et al. Invest Urol 1979), but the same protein was almost simultaneously and independently characterized in the seminal plasma (Hara et al. J Lab Clin Med 1989; Graves et al. N Engl J Med 1985). PSA is now known to be a 33-kDa glycosylated single chain serine protease (Lilja, J Clin Invest 1985; Watt et al. Proc Natl Acad Sci (U.S.A.) 1986). The 237 amino-acid polyeptide backbone has extensive similarities with that of the glandular kallikreins (Lundwall et al. FEBS Lett 1987; Schaller et al. Eur J Biochem 1987). Unlike the trypsin-like glandular kallikreins, which display Arg-restricted substrate specifity (MacDonald et al. Biochem J 1988), PSA displays chymotrypsin-like substrate specificity (Akiyama et al. FEBS Lett 1987; Christensson et al. Manuscript 1990; Lilja et al. J Biol Chem 1989). PSA has been predicted to be produced as a presumably inactive zymogen (Lundwall et al. FEBS Lett 1987). Active PSA is secreted into the seminal plasma (Lilja, J Clin Invest 1985) where it is one of the most abundant proteins of the prostate (Lilja et al. The Prostate 1988; Dubé et al. J Androl 1987). The biological activity of PSA in semen relates to its limited proteolytic fragmentation of the predominant proteins secreted by the seminal vesicles (Lilja, J Clin Invest 1985; Lilja et al. J Clin Invest 1987; McGee et al. Biol Reprod 1988).

Secondary to the release from the prostate epithelium PSA may also be detected in the circulation (Papsidero et al. Cancer Res 1980). Measurements of the serum concentration of PSA have now found widespread use in monitoring of patients with prostate cancer, although increased serum concentrations of PSA have also been reported in benign prostatic hyperplasia and secondary to surgical trauma of the prostate (Duffy, Ann Clin Biochem 1989; Brawer et al. Urology suppl 1989). However, it is presently unknown whether the immunoreactivity in serum represents the PSA-zymogen, the active PSA or PSA inactivated by extracellular proteinase inhibitors and contradictory results have been reported on the molecular mass of this immunoreactivity. Papsidero reported in 1980 the PSA-immunoreactivity to elute as a single 90 to 100 kDa peak (Papsidero et al. Cancer Res 1980), whereas Alfthan and Stenman reported the predominant part of this immunoreactivity to elute as a 30-kDa protein (Alfthan et al. Clin Chem 1988) when subjected to gel filtration chromatography.

In the proceeding invention we showed that PSA has the ability to form complexes with proteinase inhibitors that occur in high concentration in the human extracellular fluids and that PSA occurs in these fluids both in a free and complexed form. In addition, the invention proved to be very useful in diagnosis of prostate cancer patients.

SUMMARY OF THE INVENTION

According to the method of the invention, immunoassays are applied to measure free PSA as well as PSA as a proteinase inhibitor complex. Free PSA and the PSA complex are according to the invention measured by a non-competitive immunoassay employing at least two different monoclonal antibodies. The invention is further characterized by that the PSA proteinase inhibitor complex of interest is formed either with $\alpha_1$-antichymotrypsin, $\alpha_1$-protease inhibitor (API) or $\alpha_2$-macroglobulin. Moreover, the invention is characterized by that free PSA, the PSA-proteinase inhibitor complex and their ratio are applied in the diagnosis of patients with prostate cancer.

DESCRIPTION OF THE DRAWINGS

FIG. 1 shows results using polyclonal antibody, 2E9 monoclonal antibody, 2H11 monoclonal antibody and 5A10 monoclonal antibody, respectively.

FIG. 2 shows results using polyclonal antibody, 2E9 monoclonal antibody, 2H11 monoclonal antibody and 5A10 monoclonal antibody, respectively.

DETAILED DESCRIPTION

1. Production and characterization of monoclonal antibodies

Production of anti-PSA specific monoclonal antibodies Balb/c mice were immunized by intraperitoneous injections with 70 $\mu$g of PSA emulsified in equal volymes with Freund's complete adjuvant. The immunization was repeated after 3, 6 and 9 weeks with 50 $\mu$g of PSA emulsified with Freund's incomplete adjuvant. Three weeks later the mice were given a final booster with 40 μg of PSA and the mice were killed four days later. Lymphoid cells of the spleen were prepared and mixed in a 1:1 ratio with plasmacytoma cells (NS-1). The cells were fused and harvested in microtiter wells in KC-2000 (Hazleton Biologics Inc., Lenexa, U.S.A.) containing 200 g/L foetal calf serum and HAT-supplement H-0262 (1:50, Sigma) (Matikainen et al. J Gen Microbiol 1983).

Anti-PSA specific antibody production by the master clones was assayed with well strip plates coated with rabbit anti-mouse IgG (Lövgren et al. Talanta 1984). The strips were incubated with either the hybridoma supernatants or the standard (monoclonal antibody against PSA; 0812 Hybritech), washed, incubated with Eu-labelled PSA (50 ng per well), and the amount of bound Eu-labelled PSA was determined.

Cloning of the master clones by limited dilutions was performed as described (Staszewski and Yale, J Biol Med 1984). The desired clones were expanded intraperitoneally in Balb/c mice; the ascitic fluid being collected in 10 days. The IgG-fraction of the ascitic fluid was purified by chromatography on protein A-Sepharose following the protocol recommended by the manufacturer.

Solid phase bound PSA was used to test if one unlabelled monoclonal antibody could block the binding of another Eu-labelled anti-PSA MAb to the solid-phase bound PSA. The solid-phase bound PSA was obtained by the incubation of 25 μl aliquots of purified PSA (25 μg/L) and 200 μL of Assay-buffer DELFIA$^R$. (50 mmol/L Tris, pH 7.75, 0.15 mol/L NaCl, 0.5 g/L BSA, and 0.5 g/L NaN$_3$) for 2 h in well strip plates coated with the 2E9 or the 5A10 anti-PSA MAb. The strips were washed and then incubated for 1 h with 200 μL of one unlabelled anti-PSA MAb (0.005–50 μg/L). Again, the strips were washed, incubated for 1 h with another Eu-labelled anti-PSA MAb and the amount of bound Eu-labelled anti-PSA was determined.

Figure 1:
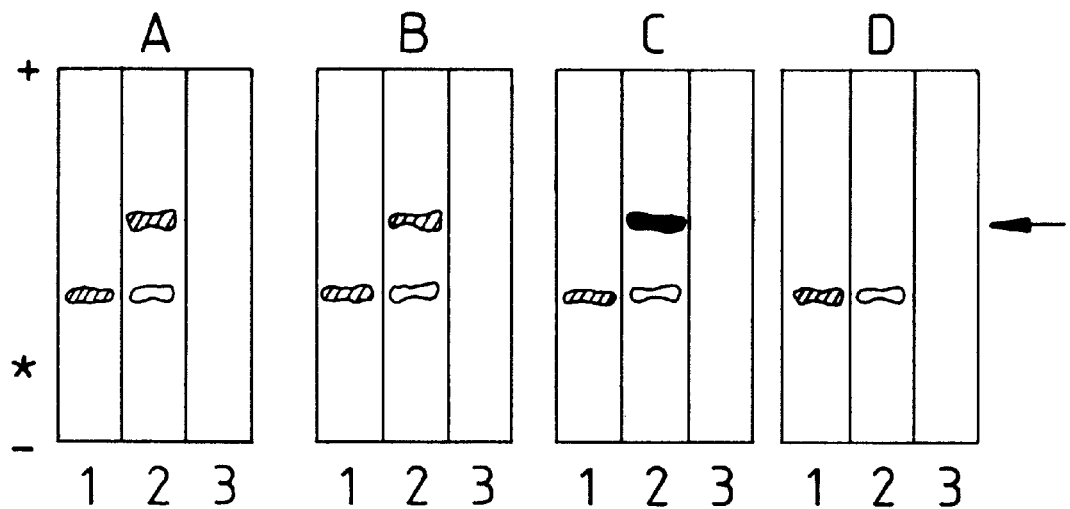
FIG. 1 presents a polyclonal antibody and three monoclonal antibodies used to probe proteins blotted onto PVDF-membranes after agarose gel electrophoresis. In lane 1 is 1 $\mu$g PSA, in lane 2 is 1 $\mu$g PSA incubated at 37° C. for 30 min with 6 $\mu$g of $\alpha_1$-antichymotrypsin, and in lane 3 is 6 $\mu$g of $\alpha_1$-antichymotrypsin.
Figure 2:
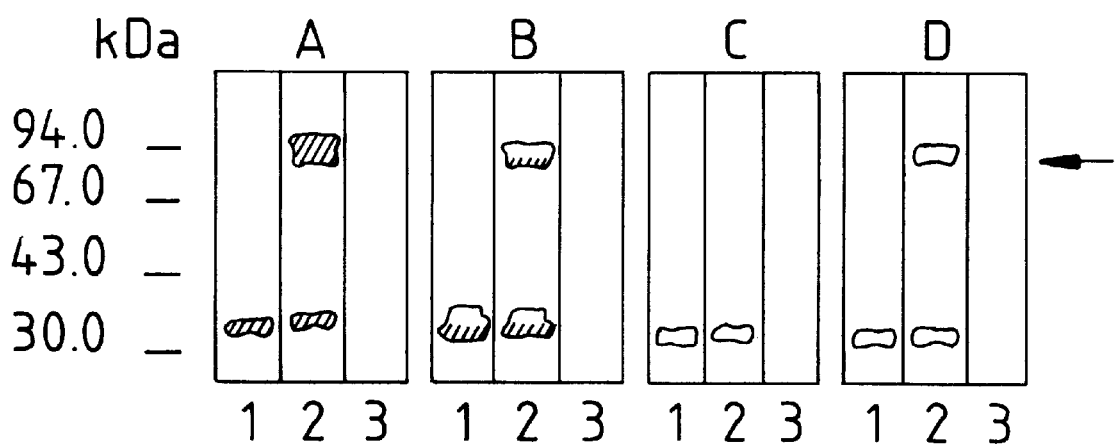
FIG. 2 presents a polyclonal and three monoclonal antibodies used to probe proteins blotted onto PVDF-membranes after SDS-PAGE. In lane 1 is 1 $\mu$g PSA, in lane 2 is 1 $\mu$g PSA incubated at 37° C. for 30 min with 6 $\mu$g of $\alpha_1$-antichymotrypsin, and in lane 3 is 6 $\mu$g of $\alpha_1$-antichymotrypsin.

Parial characterization of the epitope specificity of three monoclonal antibodies against PSA Several clones produced monoclonal antibodies against PSA as indicated by fluorometric assay. Three of these (designated 2E9, 2H11 and 5A10) were expanded and the antibodies isolated from the ascitic fluid. The three monoclonal antibodies against PSA were used to probe proteins blotted onto PVDF-membranes after agarose gel electrophoresis (FIG. 1) or SDS-PAGE (FIG. 2) of 1 μg of PSA (lane 1); 1 μg of PSA incubated at 37° C. for 30 min with 6 μg of α$_1$-antichymotrypsin (lane 2); and 6 μg of α$_1$-antichymotrypsin (lane 3). PSA blotted to PVDF-membranes from the agarose gels was identified by all three monoclonal antibodies whereas the PSA complexed to α$_1$-antichymotrypsin was identified by the 2E9 and the 2H11 antibodies but not by the 5A10 antibody. The 2E9 antibody was the only anti-PSA MAb that readily identified PSA and PSA complexed to α$_1$-antichymotrypsin when these proteins were blotted onto PVDF-membranes after SDS-PAGE. However, a minute reaction was also obtained with the PSA (but not with the PSA complexed to α$_1$-antichymotrypsin) when the 2H11 and the 5A10 antibodies were used to probe these proteins blotted onto PVDF-membranes after SDS-PAGE.

Figure 3:
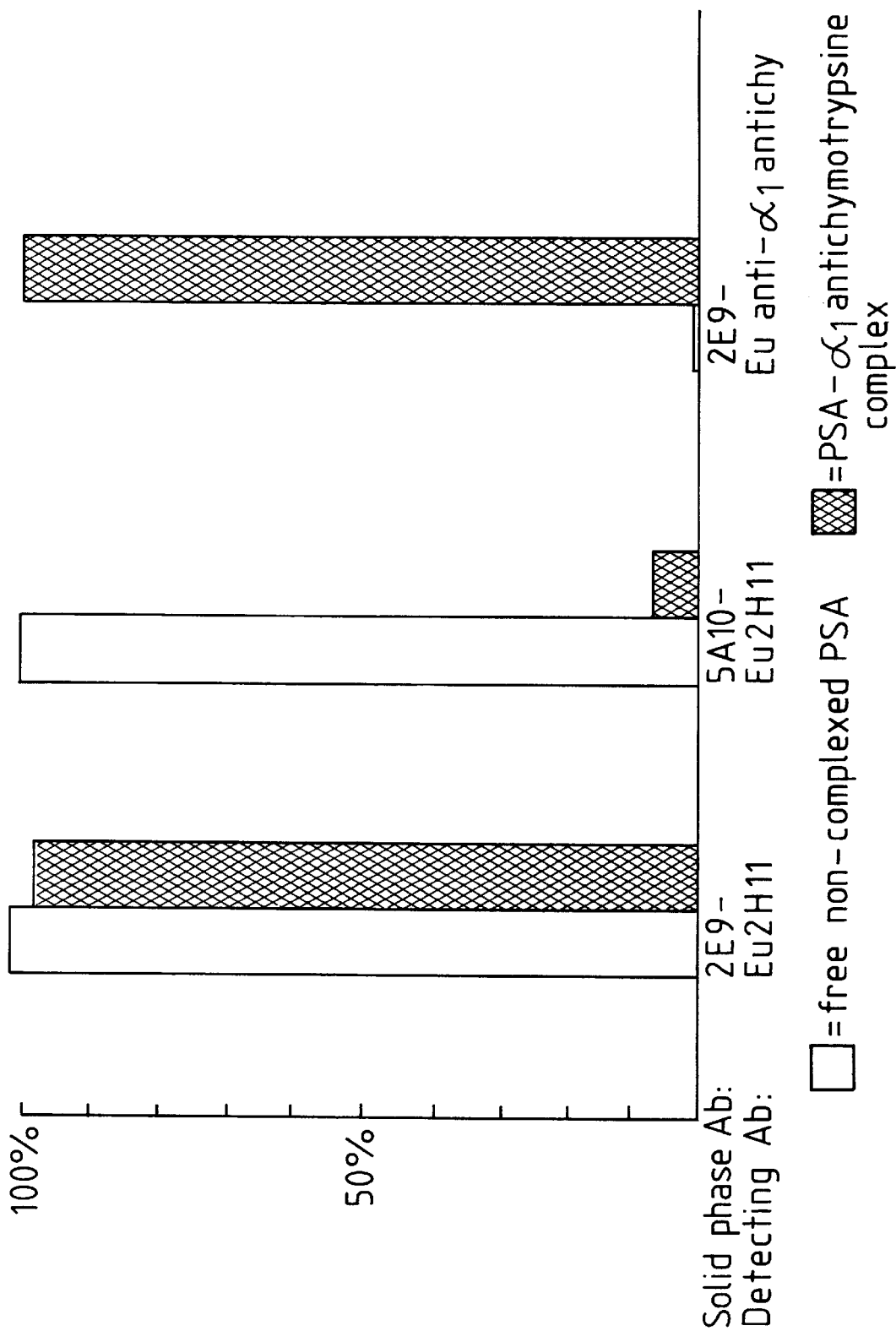
FIG. 3 presents the specificity of the three assay versions.

The epitope specificity of the three monoclonal antibodies was also characterized using three different sets of solid-phase sandwich assays. Thereby assay (A), where the 2E9 antibody was used as solid-phase catcher and Eu-labelled 2H11 was used as detecting antibody, displayed an almost identical dose-response for PSA as compared with PSA complexed to α$_1$-antichymotrypsin (Table 1; FIG. 3). This contrasts with both assay (B), where the 5A10 antibody was used as catcher and Eu-labelled 2H11 was used as detecting antibody, which prefentially recognized PSA but only poorly recognized PSA complexed to α$_1$-antichymotrypsin, and with assay (C), where the 2E9 antibody was used as catcher and Eu-labelled antibody against α$_1$-antichymotrypsin was used as detecting antibody; which only recognized PSA complexed to α$_1$-antichymotrypsin (Table 1; FIG. 3).

Solid-phase bound PSA was used to further characterize the epitope specificity of the three monoclonal antibodies against PSA; the solid-phase binding of PSA having been achieved by the use of well strip plates coated with the 2E9 or the 5A10 antibody. It was thereby found that none of the anti-PSA MAb's 2E9, 2H11 or the 5A10 significantly blocked the binding of each other when we tested the ability of one anti-PSA MAb to block the binding of another Eu-labelled anti-PSA MAb to the solid-phase bound PSA.

2. The occurance of PSA-proteinase inhibitor complexes in human serum

Analysis of PSA in human serum

Figure 4:
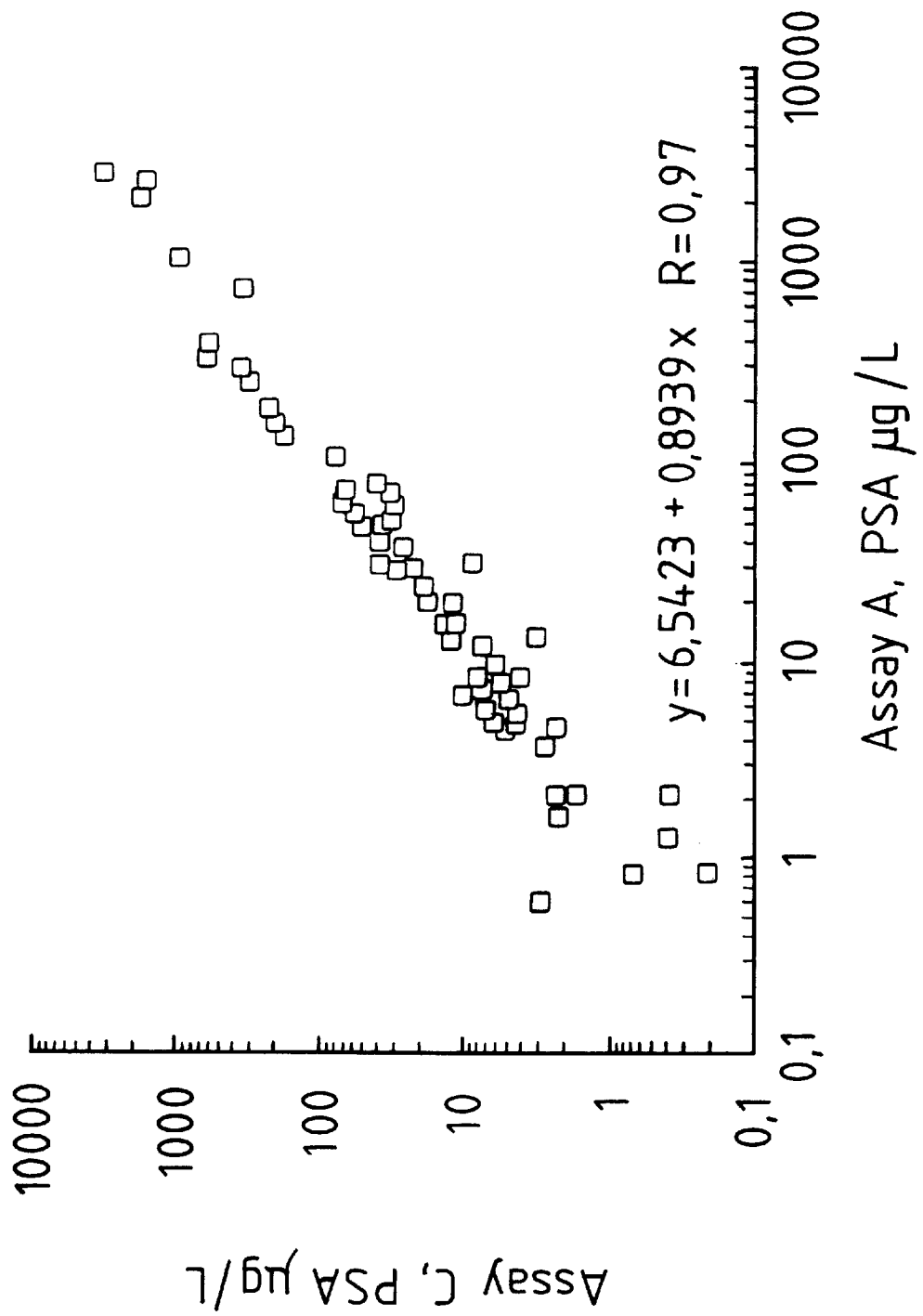
FIG. 4 presents a correlation of PSA immunoreactivity in serum samples from 65 individual patients when analyzed with assay versions A and C.
Figure 5:
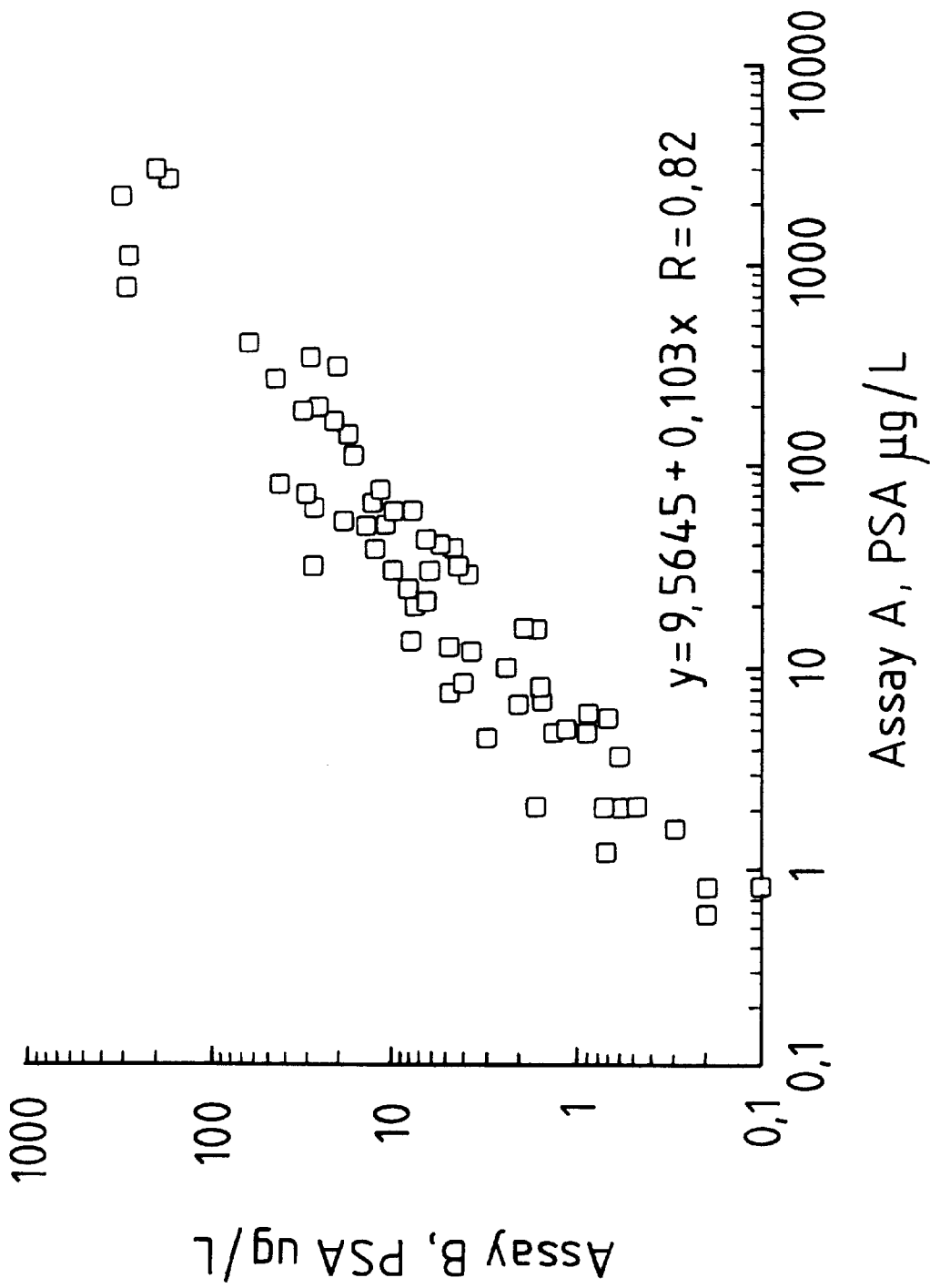
FIG. 5 presents a correlation of PSA immunoreactivity in serum samples from 65 individual patients when analyzed with assay versions A and B.

Serum from individual patient samples (n=65) were analyzed with the three different sets of assays (A, B and C). Regression analysis of the results obtained with assay A and assay C gave y=0.89x+6.55, r=0.97 (FIG. 4); and the regression analysis between assay A and assay B gave y=0.10x+9.56, r=0.82 (FIG. 5).

Figure 6:
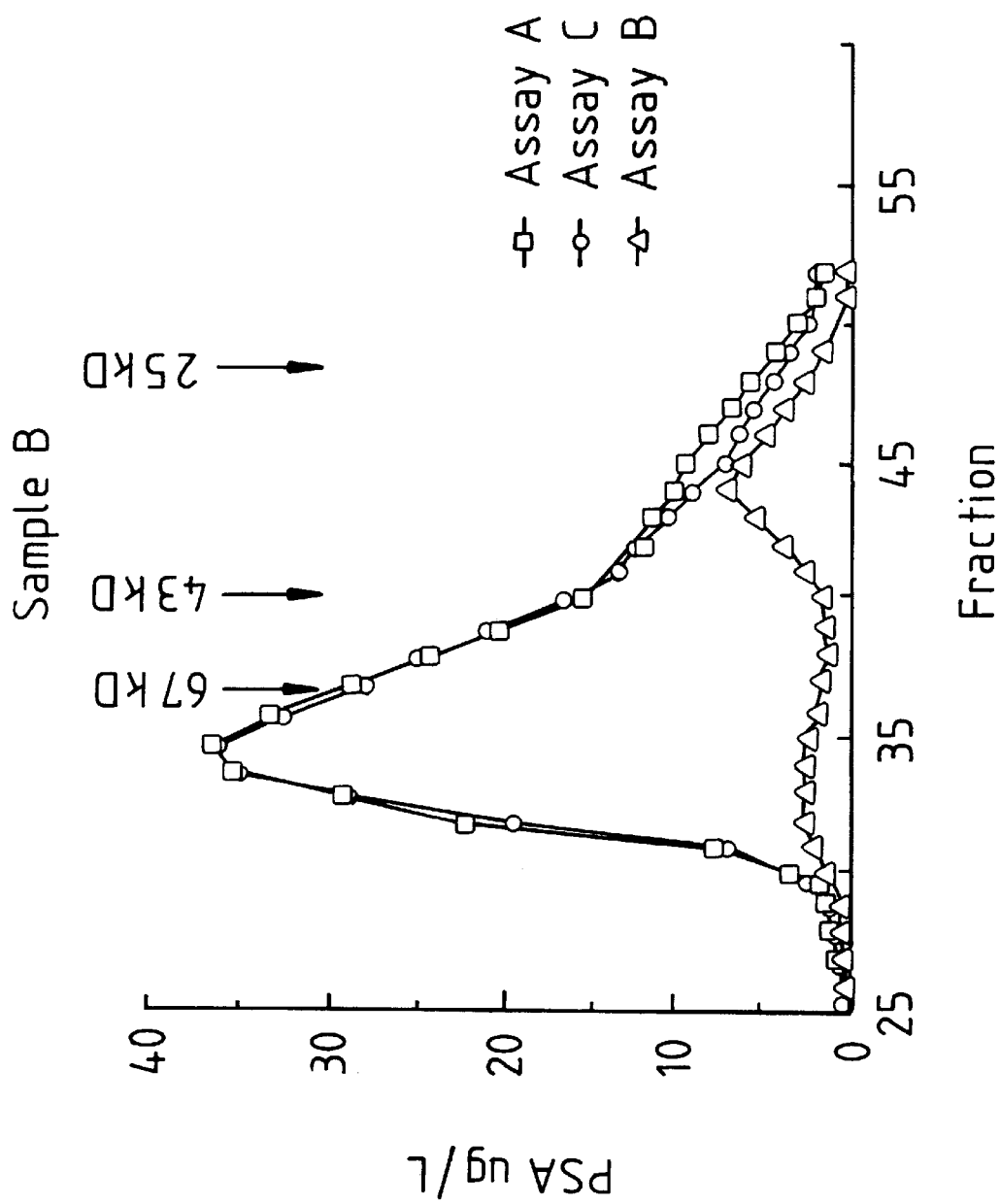
FIG. 6 presents a gel filtration of a patient sample B on a TSK 250 HPLC column. The PSA immunoreactivity of the eluted fractions were analyzed by assay versions A, B and C.
Figure 7:
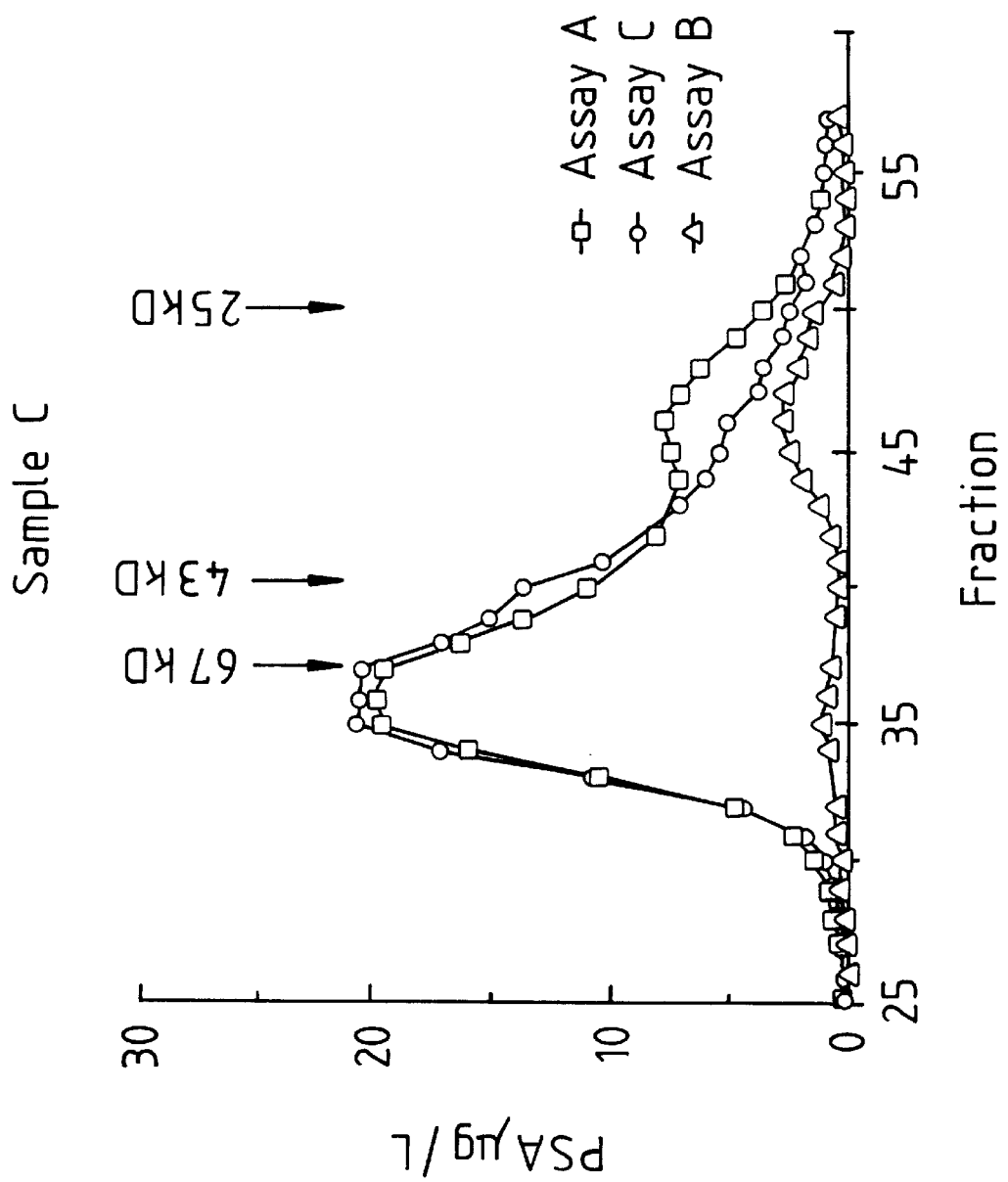
FIG. 7 presents the a filtration of a patient sample C on a TSK 250 HPLC column. The PSA immunoreactivity of the eluted fractions were analyzed by assay versions A, B and C.
Figure 8:
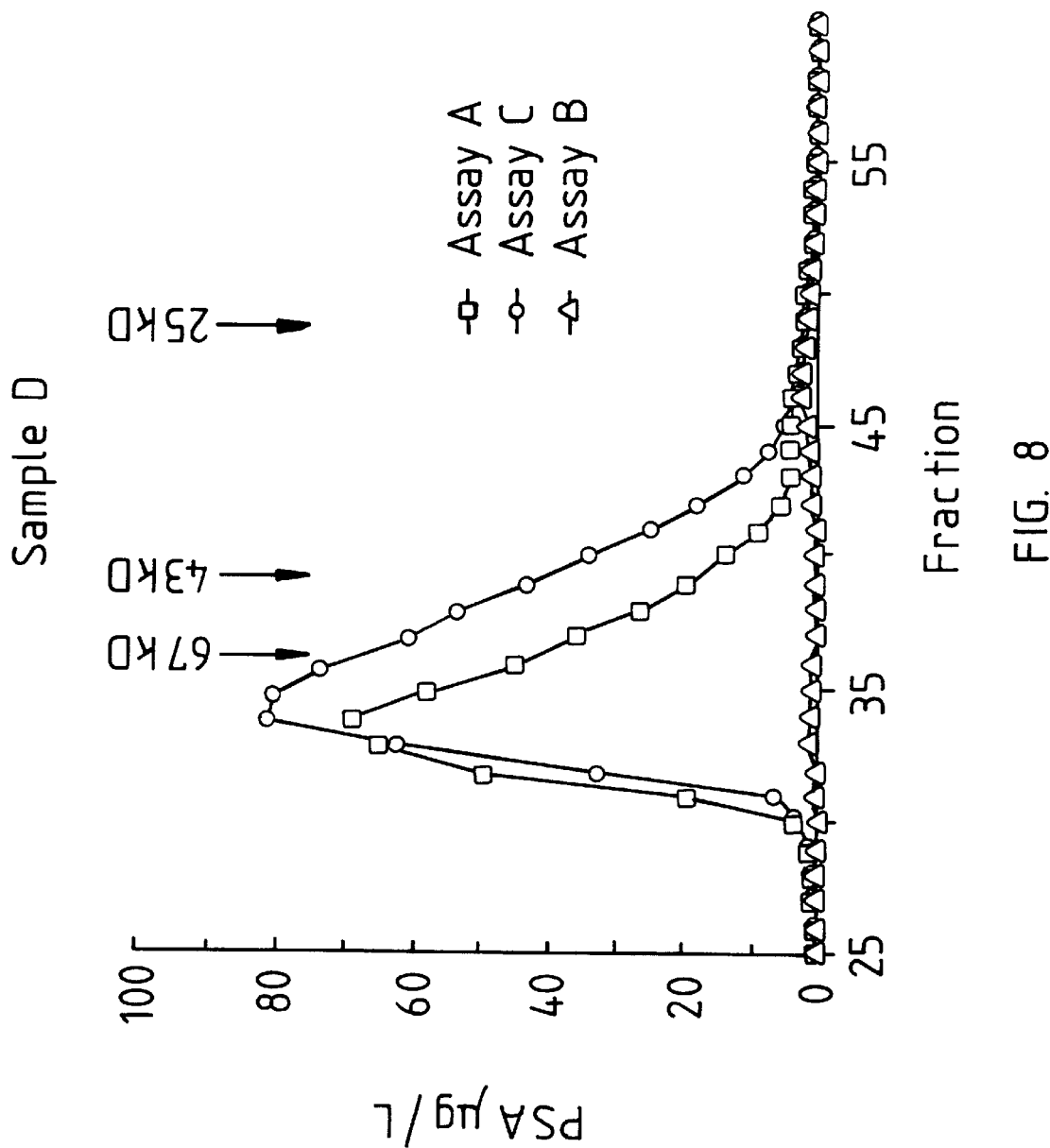
FIG. 8 presents a gel filtration of a patient sample D on a TSK 250 HPLC column. The PSA immunoreactivity of the eluted fractions were analyzed by assay versions A, B and C.

The total recovery of the immunoreactivity from the gel filtration experiments of patient samples on the TSK 250 HPLC column was equally high (82 to 107%) with all three assay procedures used (A, B and C). The-gel filtration experiments of patient samples on the TSK 250 HPLC column showed that the predominant peak of PSA-immunoreactivity, when analyzed with assay A, was identified in fractions eluting at a position corresponding to a molecular mass of 80 to 90 kDa while a minor peak of this immunoreactivity was found in fractions eluting at a position corresponding to a molecular mass of 25 to 40 kDa (FIGS. 6–8). In much the same way, the analysis of the fractions eluted with assay C (specific for PSA complexed to α$_1$-antichymotrypsin) identified one predominant immunoreactive peak in the range 80 to 90 kDa (FIGS. 6–8). However, when assay B was used to analyze the fractions eluted from the gel filtration experiments the predominant immunoreactive peak eluted at a position corresponding to mass of 25 to 40 kDa. The elution position of this peak corresponded to the minor immunoreactive peak identified with assay A (FIGS. 6–8).

Figure 9:
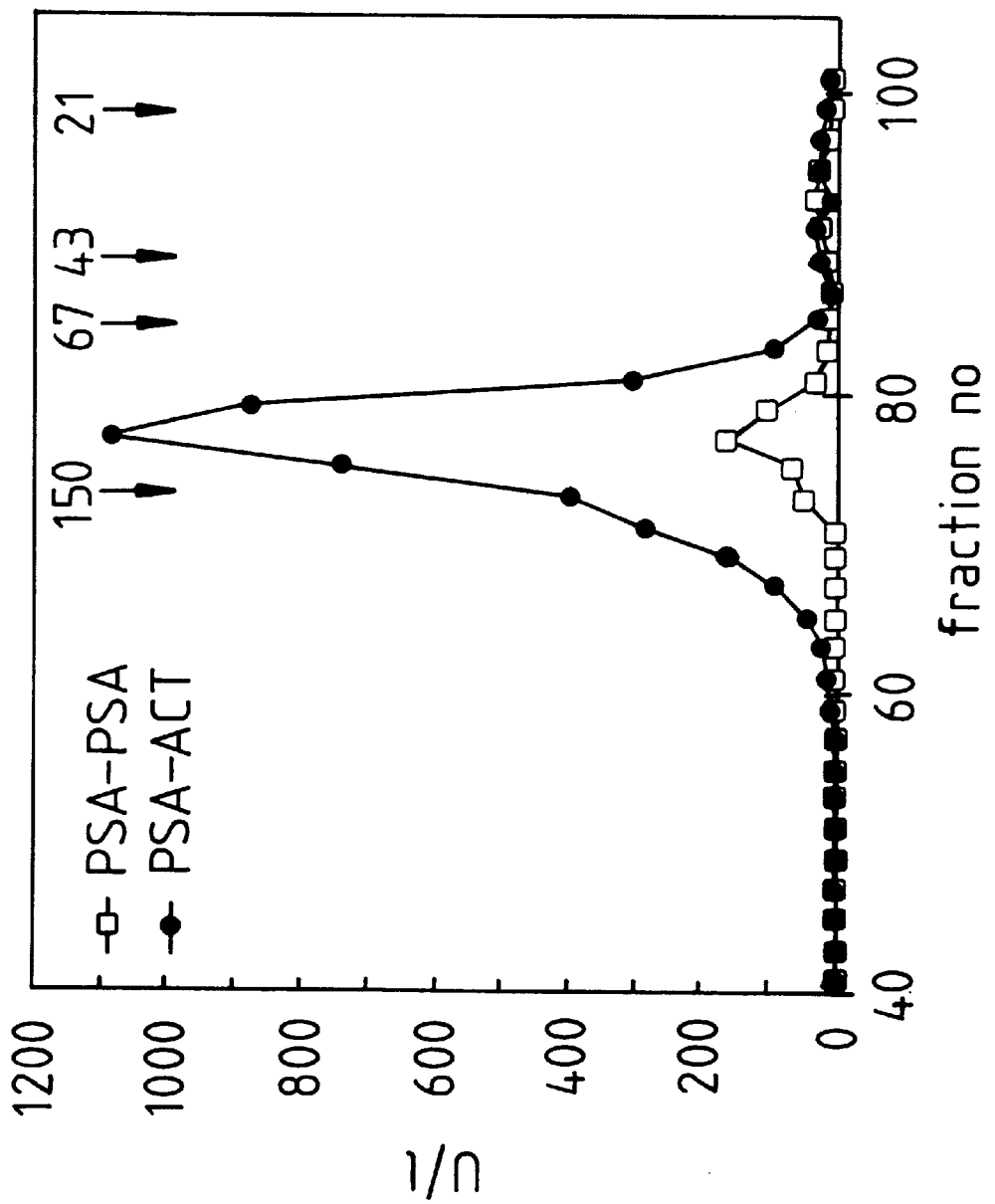
FIG. 9 presents a characterization of PSA immunoreactivity in a serum sample with a PSA level of 10000 $\mu$g/l by gel filtration. PSA and the PSA-ACT complex were measured by IFMA.
Figure 10:
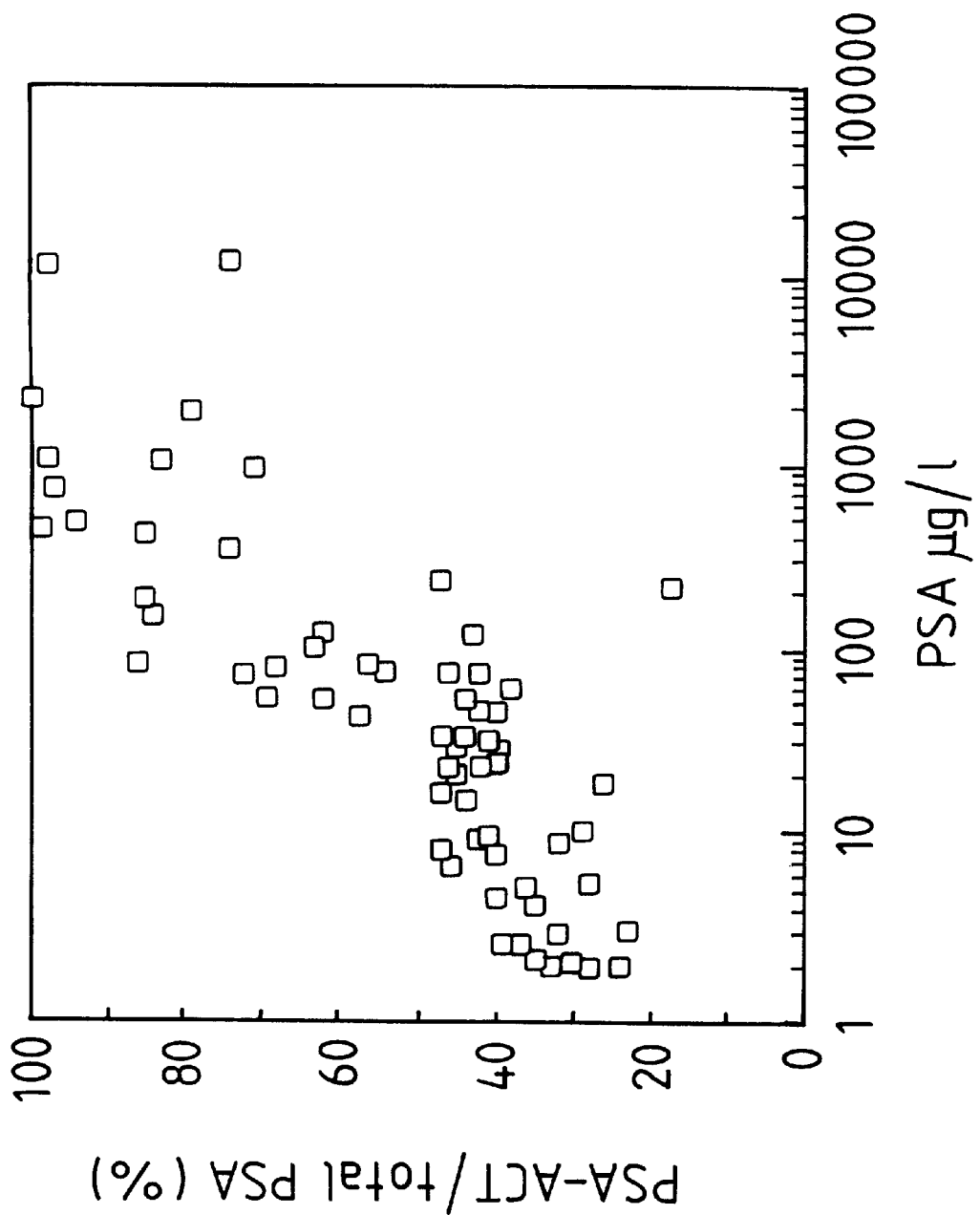
FIG. 10 presents the proportion of the PSA-ACT complex of the total PSA immunoreactivity in sera of patients with prostatic cancer as a function of the PSA concentration. The level of PSA was measured by IRMA and that of PSA-ACT by IFMA.

When serum samples from men with various levels of PSA (10–10,000 μg/L) were fractionated by gel filtration, two components corresponding to PSA and PSA-ACT were also observed. In samples with high PSA-levels the PSA-ACT complex dominated (FIG. 9). In female sera these components were not seen (not shown). The proportion of PSA-ACT of total PSA immunoreactivity increased with increasing PSA levels (FIG. 10). In sera from healthy males with PSA levels below 2.8 μg/L the proportion of PSA-ACT was 23–47%, in samples with PSA levels of 2.8–10 μg/L the proportion was 26–86% and in samples with higher levels the proportion increased further being 70–100% at PSA levels over 1000 μg/L (FIG. 10).

Figure 11:
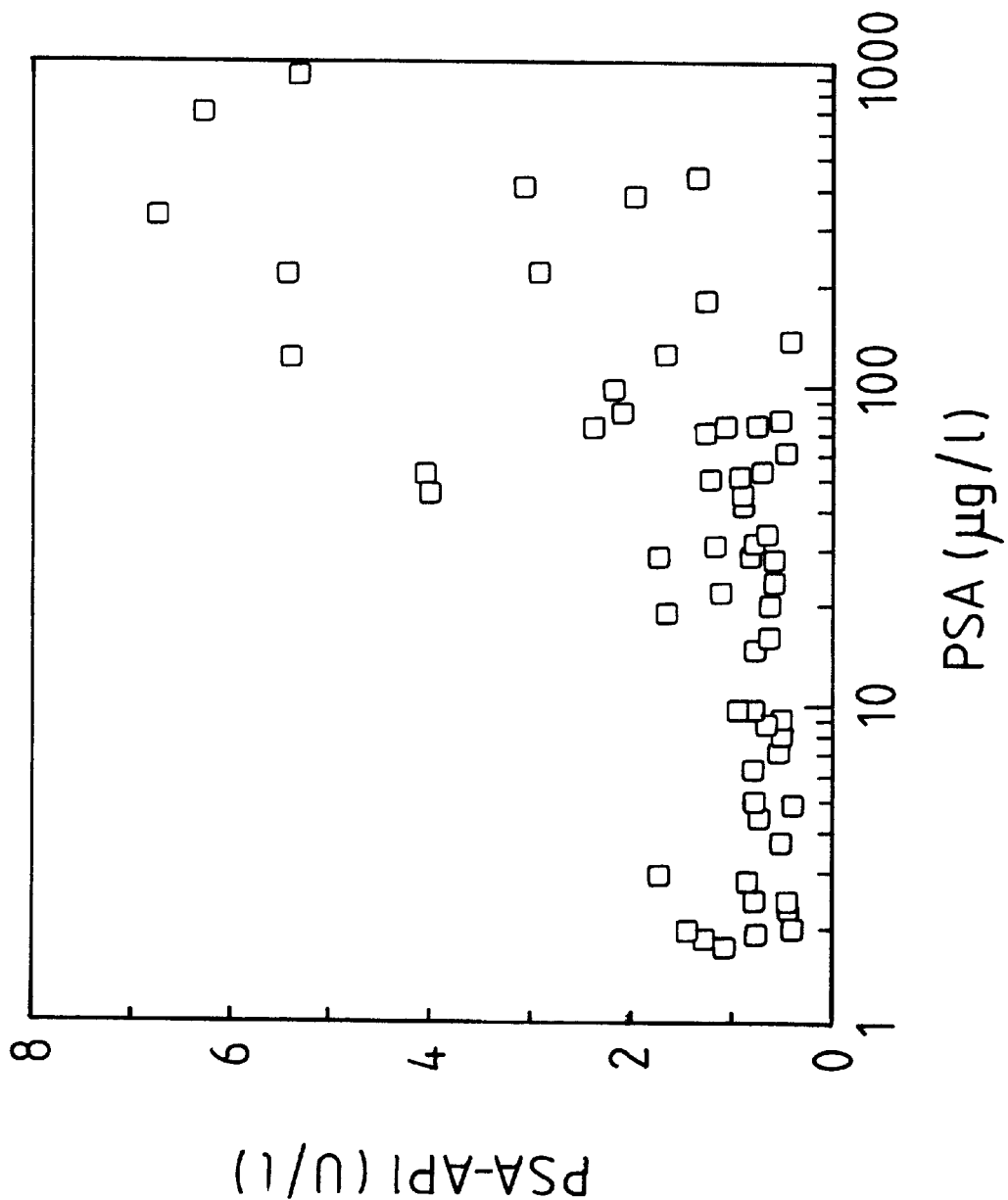
FIG. 11 presents the concentration of the PSA-API complex measured by IFMA as a function of the PSA concentration measured by IRMA in sera from patients with prostatic cancer.

On the basis of the concentrations of the complexes expressed in arbitrary units the main complex of PSA in sera was PSA-ACT complex. In samples with low PSA levels the concentration of both PSA-API and PSA-ACT were close to the detection limit. Therefore it was not possible to calculate the proportion of these complexes in normal samples. Clearly elevated levels of PSA-API complex occured in samples with PSA levels over 40 μg/L and the levels tended to increase with increasing levels of PSA (FIG. 11).

3. PSA and PSA-$\alpha_1$-antichymotrypsin complexes in the diagnosis of patients with prostate cancer The three assay versions referred to under section "Characterization of the epitope specificity of three monoclonal antibodies against PSA" were used to test 144 patients with benign prostatic hyperplasia (BPH) and 122 patients with different stages of prostate cancer (CAP). The ratios between A: PSA complexed with $\alpha_1$-antichymotrypsin/PSA total and B: PSA free non-complexed/PSA total were calculated as well as the clinical sensitivity and specificity for the measurement of total PSA and PSA $\alpha_1$-antichymotrypsin alone (Table 2). It is obvious from the presented data that increased clinical specificity is achieved by measuring the PSA $\alpha_1$-antichymotrypsin complex and that the ratios between PSA free/PSA total and PSA free/PSA complexed with $\alpha_1$-antichymotrypsin are significantly different between BPH and CAP patients.

Table 1

The table 1 presents a dose-response of purified PSA and PSA complexed to $\alpha_1$-antichymotrypsin when analyzed by three different sets of assays.

The assay A is 2E9 anti-PSA MAb as solid phase catcher and Eu-labelled 2H11 anti-PSA MAb as detecting antibody.

The assay B is 5A10 anti-PSA MAb as solid phase catcher and Eu-labelled 2H11 anti-PSA MAb as detecting antibody.

The assay C is 2E9 anti-PSA MAb as solid phase catcher and Eu-labelled rabbit antibody against $\alpha_1$-antichymotrypsin as detecting antibody.

The columns 1 indicate the purified PSA and columns 2 indicate the PSA complexed to $\alpha_1$-antichymotrypsin.

Tables 2a and 2b

The tables 2a and 2b present the results of the testing of the patient samples with three assay versions for free, complexed and total PSA. In the table BPH indicates benign prostatic hyperplasia, CAP indicates prostate cancer, G indicates the differentiation grade and T indicates the grade. The table 2b presents the sensitivity and the specifity.

TABLE 1

| PSA | PSA assay | | | | | |
|---|---|---|---|---|---|---|
| | A | | B | | C | |
| μg/L | 1 | 2 | 1 | 2 | 1 | 2 |
| 1 | 6664 | 5250 | 6733 | 2119 | 435 | 4208 |
| 5 | 26897 | 23535 | 31487 | 3179 | 487 | 15662 |
| 10 | 53452 | 41064 | 65146 | 4573 | 559 | 30283 |

TABLE 1-continued

| PSA | PSA assay | | | | | |
|---|---|---|---|---|---|---|
| | A | | B | | C | |
| μg/L | 1 | 2 | 1 | 2 | 1 | 2 |
| 100 | 534860 | 460464 | 600057 | 33006 | 2105 | 267223 |
| 500 | 2231640 | 1826790 | 2631640 | 156712 | 12073 | 726596 |

1. Purified PSA;
2. PSA complexed to $\alpha_1$-antichymotrypsin.

TABLE 2a

| | | Correlation coefficient | Ratio mean |
|---|---|---|---|
| BPH (n = 144) | A. PSA c/PSA tot | 0.932 | 0.970 |
| | B. PSA f/PSA tot | 0.853 | 0.302 |
| CAP (n = 122) | A. | 0.994 | 1.219 |
| | B. | 0.784 | 0.191 |
| CAP, G1 (n = 31) | A. | 0.994 | 1.628 |
| | B. | 0.922 | 0.190 |
| CAP, G2 (n = 47) | A. | 0.972 | 1.141 |
| | B. | 0.956 | 0.169 |
| CAP, G3 (n = 43) | A. | 0.996 | 1.014 |
| | B. | 0.818 | 0.218 |
| CAP T1-2 (n = 56) | A. | 0.985 | 1.044 |
| | B. | 0.868 | 0.178 |
| CAP T3-4 (n = 65) | A. | 0.993 | 1.372 |
| | B. | 0.770 | 0.204 |
| CAP T4 (n = 25) | A. | 0.997 | 1.174 |
| (not treated) | B. | 0.625 | 0.188 |
| BPH (n = 84) PSA ≦ 5 | A. | 0.879 | 1.059 |
| | B. | 0.850 | 0.301 |
| BPH (n = 60) PSA > 5 | A. | 0.888 | 0.846 |
| | B. | 0.735 | 0.303 |
| CAP (n = 26) PSA ≦ 5 | A. | 0.913 | 1.773 |
| | B. | 0.826 | 0.202 |
| CAP (n = 94) PSA > 5 | A. | 0.993 | 1.065 |
| | B. | 0.778 | 0.188 |
| CAP (n = 25) | A. | 0.919 | 1.025 |
| PSA > 5 ≦ 20 | B. | 0.502 | 0.187 |
| CAP (n = 69) | A. | 0.993 | 1.080 |
| PSA > 20 | B. | 0.770 | 0.184 |

TABLE 2b

| | Sensitivity and specificity | | | |
|---|---|---|---|---|
| PSA tot | Sensitivity | PSA tot | >5 | 95/121 = 0.785 |
| | | | >10 | 80/121 = 0.661 |
| | Specificity | PSA tot | <5 | 84/144 = 0.583 |
| | | | <10 | 116/144 = 0.806 |
| PSA c | Sensitivity | PSA c | ≧5 | 93/121 = 0.769 |
| | | | ≧10 | 81/121 = 0.669 |
| | Specificity | PSA c | <5 | 92/144 = 0.639 |
| | | | <10 | 124/144 = 0.861 |

We claim:

1. An isolated PSA-proteinase inhibitor complex wherein the proteinase inhibitor is $\alpha_2$-macroglobulin.
2. An isolated PSA-proteinase inhibitor complex wherein the proteinase inhibitor is $\alpha_1$-antichymotrypsin.

\* \* \* \* \*